United States Patent [19]

Ryan et al.

[11] Patent Number: 4,652,756

[45] Date of Patent: Mar. 24, 1987

[54] AUTOMATED ACOUSTO-OPTIC INFRA-RED ANALYZER SYSTEM FOR MONITORING STACK EMISSIONS

[75] Inventors: Frederick M. Ryan, Loyalhanna Twp., Westmoreland County, Pa.; Robert L. Nelson, Orrville, Ohio

[73] Assignee: Westinghouse Electric Corp., Pittsburgh, Pa.

[21] Appl. No.: 736,199

[22] Filed: May 20, 1985

[51] Int. Cl.$^4$ .................. G02F 1/11; G01N 21/35
[52] U.S. Cl. .................. 250/343; 250/338; 250/339; 350/372
[58] Field of Search ............... 250/339, 338 GA, 341, 250/343; 350/372

[56] References Cited

U.S. PATENT DOCUMENTS 3,644,015  2/1972  Hearn .................................. 350/372
4,421,411  12/1983  Ida ...................................... 250/339

*Primary Examiner*—Carolyn E. Fields

*Attorney, Agent, or Firm*—Thomas R. Trempus

[57] ABSTRACT

An improved automated acousto-optic analyzer system includes an acousto-optic tunable filter which is coupled with a source of radiation to produce pulsed light at predetermined wavelengths. This light is transmitted through a gas stack containing gases to be analyzed, to a distant detector. The configuration of the acousto-optic tunable filter, radiation source on one side of an environment of interest and a detector on the opposite side of an environment of interest produces spatial separation of the tuned, diffracted light from the undiffracted broad spectrum of the light source at the detector. This configuration eliminates the need for polarizers in the system. It also combines the tuning function of the AOTF with a chopping function, allowing extraneous radiation to be discriminated against. Thus the improved configuration of the disclosed invention permits effective operation of the gas analysis system in a gas stack characterized by extremely high ambient temperatures.

6 Claims, 2 Drawing Figures

AUTOMATED ACOUSTO-OPTIC INFRA-RED ANALYZER SYSTEM FOR MONITORING STACK EMISSIONS

FIELD OF THE INVENTION

The present invention relates to infra-red analyzers. In particular, the present invention is directed to an improved automatic acousto-optic infra-red analyzer system which is particularly well suited for use in monitoring stack gas emissions.

BACKGROUND OF THE INVENTION

A large and growing market exists for analytical devices which can be used to analyze the reaction products of a wide variety of industrial processes. In addition, on-line real time combustion product analyzers are needed to facilitate more efficient burning of hydrocarbon fuel. For example, the electric utility has been faced with the task of monitoring stack emissions for some years. At first, this consisted of measuring the oxygen concentration for controlling combustion efficiency, and of monitoring smoke opacity. Further regulations have led to the necessity of monitoring sulfur oxides and nitrogen oxides. Additional gases will undoubtedly also require monitoring in the future. Proposed regulations in Europe, for example, will require the monitoring of ammonia if it is added to the stack to maintain precipitron efficiency. Recent studies have shown that increased combustion efficiency can be achieved if carbon monoxide is monitored. The list of gases is rapidly growing to larger and larger numbers. The historical solution has been to install a separate sensor to monitor each gas. This approach becomes more and more expensive and a less desirable approach as the total number of gases for which monitoring is required increases.

It is known to employ analytical devices which utilize ultraviolet and infra-red spectrophotometry, as well as gas and liquid chromatography in order to meet the industrial needs outlined above. Such optical instruments as well as the system of the present invention utilize the following important characteristics of materials. A particular molecule has a characteristic absorption spectrum which is dissimilar to that of all other molecules. The spectra of mixtures of molecules are additive and the absorption is proportional to the concentrations of the molecules. Optical absorption spectra can be obtained from any type of sample be it solid, liquid, or gas so long as the sample is optically transmissive, and the spectra can be obtained in a non-destructive testing of the sample. Almost all gas molecules absorb infra-red radiation. Each molecule has its absorption at specific characteristic wavelengths, so that by monitoring the magnitude of the absorption at the specific wavelengths, the amount of gas present in the stack may be deduced. This is accomplished by transmitting infra-red radiation across the stack to a detector. The wavelength of the transmitted radiation is tuned to coincide with the specific wavelength of the gas to be measured. The strength of the detector signal at a given wavelength correlates with the concentration of the absorbing gas at that wavelength. The selective tuning of the infra-red radiation is accomplished either by inserting narrow band interference filters in the path, or by inserting cells containing appropriate gas fills in the path. Both of these approaches involve mechanical motion, and the number of cells or filters that can be employed is obviously limited. Thus reliability and accuracy suffer from the less than ideal properties of these tuning elements.

It has recently been recognized that certain birefringent optical materials which are termed acousto-optic materials can be used as a filter in a spectrum analyzer. In such acousto-optic materials, a light beam propagating as an E-ray can under certain conditions be converted into an O-ray by interaction with, and diffraction from, an acoustic wave propagating from the same medium. This phenomenon has been used in fabricating narrow band optical filters, the peak transmission wavelength of which can be selected by properly choosing the frequency of the acoustic wave. Even more recently, new efficient infra-red transmissive acousto-optic materials such as thallium-arsenic-selenide, as described in U.S. Pat. No. 3,792,287 which is owned by the assignee of the present invention and incorporated herein by reference, provide the possibility of operation over the near to mid-infra-red spectrum from about 1 micrometer to about 16 micrometers.

An automated acousto-optic infra-red analyzer system which utilizes acousto-optic technology is described in U.S. Pat. No. 4,490,845 which is assigned to the assignee of the present invention and incorporated herein by reference as it fully set forth. U.S. Pat. No. 4,490,845 teaches an automated acousto-optic tunable filter infra-red analyzer system which permits rapid electronic tuning of the filter to a selected infra-red bandpass via the acousto-optic interaction with infra-red radiation which has passed through a sample. The infra-red analyzer system includes means for directing infra-red radiation through the sample to be analyzed, which sample has a predetermined infra-red absorption characteristic. Means are provided for directing the infra-red radiation through an acousto-optic tunable filter after the infra-red radiation has passed through the sample species. An acousto-optic tunable filter includes an input polarizer for selectively polarizing the infra-red radiation. The tunable filter includes an optically aligned acousto-optic crystal through which the selectively polarized infra-red radiation is passed at a predetermined angle relative to the crystal optic axis. An acoustic transducer means is coupled to the crystal and to a variable frequency RF energy source whereby acoustic waves are launched in the crystal in order to interact with the selected narrow bandwidth portion of the polarized infra-red radiation to make it distinguishable from the remaining radiation. The tuned or selected narrow bandwidth radiation is a function of the frequency of the RF energy source which is connected to the acoustic transducer of the filter. Infra-red radiation detection means are coupled to the filter to detect the output filtered infra-red radiation and to generate an output signal as a function of the output filtered infra-red radiation. Automated computing means are provided, with the detection means output electrical signal applied to the computing means for determining the sample species present in the sample. The computing means includes means for selectively activating the RF energy source to determine the timing and frequency of RF energy applied to the acoustic transducer to thereby determine the selected or filtered narrow bandwidth infra-red wavelength of interest.

It is an object of the present invention to provide an improved automated acousto-optic infra-red analyzer system which is particularly well suited for the task of monitoring stack gas emissions. The improved analyzer system is an electronically operated device that easily interfaces with a microcomputer for "smart sensor" applications such as rapid scan differential absorption spectroscopy, signal conditioning, and comparison of measured absorption spectra with stored spectra.

It is a further object of this invention to provide an improved automated acousto-optic infra-red analyzer system in which the infra-red detector and the acousto-optic tunable filter are separated so that the angular displacement of the narrow-band interacted radiation is adequate to separate it spatially from the broad-band non-interacted radiation at the detector, thus eliminating the need for crossed polarizers.

It is yet another object of this invention to provide an improved automated acousto-optic infra-red analyzer system with a configuration in which the AOTF is transmitting narrow-band pulsed or chopped radiation across the gas containing stack to the detector. Thus, the detector can discriminate between these pulsed emissions and the steady thermal emissions from the hot stack. Accordingly, the improved analyzer system is particularly well suited for use in applications in which the gas to be analyzed is of a very high temperature.

It is yet another object of this invention to provide an analyzer system which has the potential for inexpensive manufacture and is a solid state device having no moving parts and therefore a very high level of reliability.

It is still another object of this invention to provide an improved automated acousto-optic infra-red analyzer system capable of infinitely variable wavelength selection which can be used to measure any required gas within an environment of interest.

It is still another object of this invention to provide an improved automated acousto-optic infra-red analyzer system which is capable of covering the entire infra-red region which is useful for measuring gas absorptions.

SUMMARY OF THE INVENTION

This invention provides an improved broad-band automated acousto-optic tunable filter multi-gas infra-red analyzer system which permits rapid electronic tuning of the filter to a selected infra-red bandpass via the acousto-optic interaction with infra-red radiation passed through an environment of interest in order to detect the presence of a particular species within that environment. The infra-red analyzer system includes means for directing infra-red radiation through an environment of interest which may contain the species to be analyzed, which species have predetermined infra-red absorption characteristics. Means for directing the infra-red radiation upon the acousto-optic tunable filter prior to modification of the infra-red radiation by the absorption characteristics of a species are provided. The acousto-optic tunable filter comprises an optically aligned acousto-optic crystal through which the infra-red radiation is passed at a predetermined angle relative to the crystal optic axis, an acoustic transducer means coupled to a variable frequency RF energy source and to the acousto-optic crystal to launch acoustic waves into the crystal to interact with a selected narrow bandwidth portion of the radiation in order to make it distinguishable from the remaining infra-red radiation, which selected narrow bandwidth portion is a function of the frequency of the RF energy and acoustic waves. The selected narrow bandwidth portion is angularly displaced with respect to the nonselected or noninteracted-with infra-red radiation passed through the acousto-optic tunable filter. Infra-red radiation detection means are provided which detect the angularly displaced, selected narrow bandwidth portion of the infra-red radiation after having passed through the environment of interest. The detector means generates an output electrical signal which is a function of the detected radiation. The detection means is disposed in relation to the AOTF such that the angular displacement of the selected narrow bandwidth portion is adequate to separate it spatially from the nonselected radiation at the detector means. Finally, computing means to which the detection means output electrical signal is applied, is provided for determining the species present in the sample cell and includes means for the pulsed operation of the RF energy source to determine the timing and frequency of RF energy applied to the acoustic transducer mated to the acousto-optic crystal to determine the infra-red wavelength selectivity or tuning of the acousto-optic tunable filter. As a result, the AOTF is transmitting narrow-band pulsed radiation across the gas containing volume to the detector. This allows the detector to discriminate between these pulsed emissions and a steady thermal emission from the hot stack.

BRIEF DESCRIPTION OF THE DRAWINGS

The above as well as other features and advantages of the present invention can be readily appreciated through consideration of the detailed description of the preferred embodiment in conjunction with the several drawings in which.

DESCRIPTION OF THE PREFERRED EMBODIMENT

Figure 1:
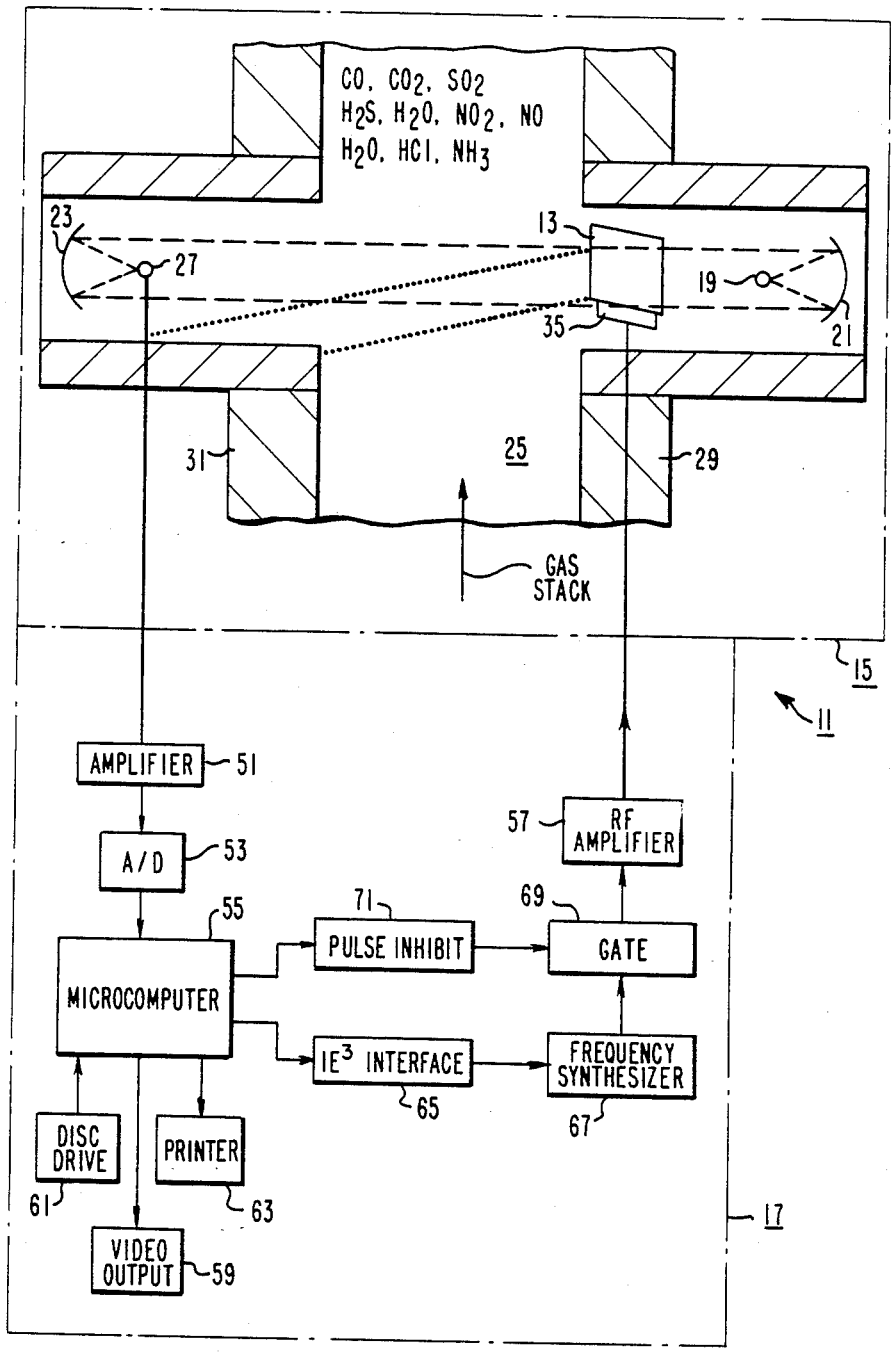
FIG. 1 is a schematic illustration of an embodiment of the improved automated acousto-optic infra-red analyzer system according to the teachings of the present invention.

An improved automated acousto-optic tunable filter infra-red analyzer system is generally indicated by the reference character 11 and is seen in FIG. 1 configured from the several subsystems and components including an acousto-optic tunable filter (AOTF) 13. The improved analzyer system 11 can be viewed as having two major subsystems, an optical system 15 and an electronic system 17. The optical system 15 of the analyzer system 11 is essentially an infra-red solid-state spectrometer which has been designed to permit operation over a relatively wide spectral range. An infra-red radiation source 19 such as a Nernst glower is used as the primary source of broad-band infra-red radiation for the system. A portion of the output infra-red radiation from the source 19 is collected and collimated by a mirror 21. The collimated beam from the mirror 21 is passed through the AOTF 13 in which a narrow bandwidth portion of the radiation is selected and distinguished from the remaining infra-red radiation as shown in the dot-lines of FIG. 1. A second mirror 23 is aligned so as to collect the spatially separated narrow band interacted radiation output from the AOTF 13 after it passes through an environment of interest generally indicated at 25 and directs the collected collimated beam to a detector means 27. It is of course possible to utilize other techniques to direct the infra-red radiation to the input face of the acousto-optic tunable filter without departing from the basic concepts of this invention. The environment of interest in this particular application is a gas stack of, for example, an industrial processing plant or a utility, generally indicated at 25. As can be seen from the schematic illustration of FIG. 1, the gas stack 25 includes opposed sidewalls 29 and 31. In this configuration the detector 27 and the AOTF 13 are placed on opposite sides of the stack 25. By separating the detector and the AOTF, the angular displacement of the narrow-band interacted radiation is adequate to separate it spatially from the broad-band noninteracted radiation at the detector. This provides a specific improvement over the system disclosed in U.S. Pat. No. 4,490,845 as discussed above, in that the need for crossed polarizers is eliminated.

Figure 2:
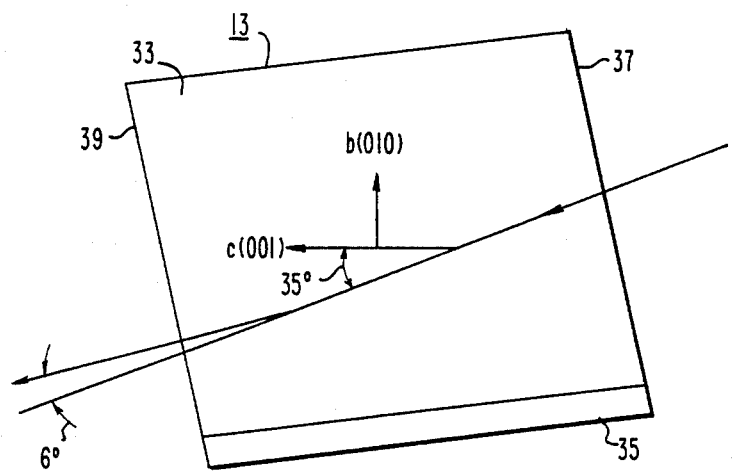
FIG. 2 is an enlarged representation of the acousto-optic tunable filter of the present invention illustrating the angular displacement of the narrow-band interacted radiation with respect to the broad-band noninteracted radiation which passes therethrough.

The acousto-optic tunable filter 13 operates through the interaction of acoustic waves with light waves in a suitable crystal 33. Typically an acoustic transducer 35 is bonded to the optical crystal 13 and is driven by a controllable RF signal as will be described hereinafter. Various optical materials have been developed for use in acousto-optic devices, these materials include thallium-arsenic-selenide as described in U.S. Pat. No. 3,792,297, thallium-phosphorus-selenide per U.S. Pat. No. 3,929,970 and thallium-arsenic-sulfide per U.S. Pat. No. 3,799,659 all assigned to the assignee of the present invention and incorporated herein by reference. The crystal 33 has a relatively large and constant index of refraction. The transducer 35 is bonded to the side of the crystal 33 generally normal to the incoming light beam. The acoustic transducer 35 consists of an X-cut lithium niobate crystal plate which is attached to the acousto-optic crystal with an indium metal bond. A conductive electrode pattern is provided on both sides of the lithium niobate transducer. The electrode is driven from the electronic system as will be described hereinafter. The input optical face 37 of the crystal 33 is cut so as to be normal to the incident infra-red beam, while the output beam is diffracted at an angle of about 6° to the incident beam, and the exit optical face 39 is cut so as to be normal to this diffracted beam. The acousto-optic crystal 33 is designed such that the crystalline b-c axes are contained in the optical plane of incidence of the crystal and the optical beam is propagated at a selected angle. The acoustic energy from the transducer 35 is propagated nearly normal to the optical beam propagation direction. When RF power is applied to the transducer, the input infra-red radiation is propagated along a path at a predetermined angle to the optic axis of the crystal and a narrow passband frequency selectively interacts with the acoustic wave. The selected or tuned narrow passband infra-red radiation is also distinguishable from the remaining input radiation because it is shifted or diffracted at a small angle relative to the unaffected input radiation path. Typically this is about a 6° offset. Thus the filtered light is separated spatially due to this offset angle. A thallium arsenic selenide acousto-optic crystal has a base plan which contains the crystalline b-c axes and the optical beam is propagated at about 35° relative to the crystallographic c or optic axis as shown in FIG. 2. This angular relationship between the input radiation and the crystalline c or optic axis is not critical and can be varied, but variation can affect the specific RF tuning frequency which is used to filter or tune and desired bandwidth wavelength of interest.

The electronic system 17 as illustrated in FIG. 1, will now be described. The analog output single from the infrared detector 27 is fed to an amplifier 51 and to analog to digital converter 53 with the resultant digital signal applied to microcomputer 55. The electrical system 17 interfaces with the optical system 15 at the acousto-optic tunable filter 13 via the transducer 35 which is connected to the RF amplifier 57 from which selected frequency RF drive power is applied via the transducer 35 to launch acoustic waves into the crystal 33. In this way optically filtered infra-red radiation can be detected and utilized by the microcomputer to determine the absorption resulting from the presence of selected gases in the gas stack 25. The microcomputer 55 typically has a video output means 59 associated therewith for visual display of the detected signals, as well as memory means 61 and a printer 63. The memory means 61 stores the control and operation signal for the system. The microcomputer 55 through an appropriate interface means 65, when supplied with control signals from the memory means 61, controls the output frequency and amplitude from a frequency synthesizer 67 which is connected by a gate means 69 to the RF amplifier 57 for pulsed operation. The gate 69 is utilized in conjunction with a pulse inhibit circuit means 71 to provide assurance that the RF pulse of the proper width is applied to the transducer while the RF power duty cycle is limited to a load level which does not overheat the crystal 33. This system is thus capable of operating not only as a rapidly tunable narrow band infra-red filter but also as a solid state optical chopper as well.

Control signals from memory means 61 are applied to the microcomputer 55 in order to sequentially supply RF pulses typically about 3.5 microseconds long at about 10 watts peak power over the operating frequency range of about 20 to 100 megahertz to the transducer 35 of the acousto-optic tunable filter 13. The pulses are designed to cause the filter to be transmissive at a reference wavelength where there is no absorption and then at a wavelength where a known gas has a relatively strong absorption. In addition to rapidly sampling the absorption wavelength for a variety of gases the system is initialized with no gas present to yield the sample amplitude signal as measured by the analog to digital converter for the reference wavelength and at a gas absorption wavelength. The microcomputer can then be utilized to generate feedback process control signals as a function of the analysis to control the particular process such as combustion which is being analyzed.

The system has been utilized in sampling conventional combustion product gases such as carbon dioxide which is sampled when RF frequency of 41 megahertz is applied and the resulting passband wavelength indicative of carbon dioxide is at 4.2 micrometers. For nitric oxide the RF frequency is 36 megahertz yielding a passband wavelength of 5.2 micrometers. For carbon monoxide, an RF frequency of 37 megahertz yields a passband wavelength of 4.7 micrometers, while for methane and RF frequency of 53 megahertz yields a passband wavelength of 3.39 micrometers. For sulfur dioxide, an RF frequency of 44 megahertz yields a passband wavelength of 4.0 micrometers.

What has been described is an improved automated acousto-optic analyzer system in which the infra-red radiation source and acousto-optic tunable filter are disposed on one side of a gas stack and a infra-red detector is disposed on the opposite side of that stack. By separating the detector from the acousto-optic tunable filter, the annular displacement of the narrow-band interacted radiation is adequate to separate it spatially from the broad-band noninteracted radiation at the detector, thus eliminating the need for polarizers. This configuration provides a second improvement in that the acoustooptic tunable filter is transmitting narrow-band pulsed or chopped radiation across the gas containing volume to the detector. The detector can discriminate between these pulsed emissions and the steady thermal emissions from the hot stack. Thus this configuration of the AOTF, radiation source, and detector produces spatial separation of the tuned, diffracted light from the undiffracted broad spectrum of the light source at the detector, and combines the tuning function of the AOTF with a chopping function, allowing extraneous radiation to be discriminated against.

What is claimed is:

1. An improved broad-band automated acousto-optic tunable filter multi-gas infra-red analyzer system comprising:

means for directing infra-red radiation through an environment of interest containing species to be analyzed, which species have predetermined infra-red absorption characteristics;

an ascousto-optic tunable filter comprising an optically aligned acousto-optic crystal through which the infra-red radiation is passed at a predetermined angle relative to the crystal optic axis, an acoustic transducer means coupled to a variable frequency RF energy source and to the acousto-optic crystal to launch acoustic waves in the crystal to interact with a selected narrow bandwidth portion of the radiation to make the selected narrow bandwidth portion distinguishable from the remaining infrared radiation, which selected narrow bandwidth portion is a function of the frequency of the RF energy and acoustic waves, said selected narrow bandwidth portion being made distinguishable by being angularly displaced with respect to the non-selected infra-red radiation passed through said acousto-optic tunable filter;

means for directing the infra-red radiation upon said acousto-optic tunable filter prior to modification of the infra-red radiation by the absorption characteristics of a given species within the environment of interest;

infra-red radiation detection means which detects the angularly displaced, selected narrow bandwidth portion of the infra-red radiation after the angularly displaced selected narrow bandwidth portion has passed through the environment of interest, and which detection means generates an output electrical signal as a function of the detected radiation said detection means being disposed in relation to said acousto-optic tunable filter such that the angular displacement of the selected narrow bandwidth portion is adequate to separate it spatially from the broad-band non-selected radiation at said detection means; and computing means to which the detecting means output electrical signal is applied for determining the species present in the environment of interest, and including means for the pulsed operation of the RF energy source to determine the timing and frequency of RF energy applied to the acoustic transducer means mated to the acouto-optic crystal to determine the infra-red wavelength selectivity or tuning of the acousto-optic tunable filter, wherein the pulsed operation permits discrimination by said detection means between pulsed emission means of the selected narrow bandwidth portion and emissions from the environment of interest.

2. The improved analyzer system set forth in claim 1 wherein the computing means includes a microprocessor and memory means for comparing the detected signal to predetermined molecular species indicative signals stored in the memory means, and wherein the memory means provides a predetermined sequence of signals which are applied to the microprocessor to be applied to a frequency synthesizer to vary the frequency of the RF energy applied to the acoustic transducer means coupled to the acousto-optic crystal to vary the selection of the narrow bandwidth portion of the infra-red radiation which is analyzed, and wherein predetermined frequencies corresponging to predetermined molecular sample species are applied.

3. The improved analyzer system set forth in claim 1 wherein the RF energy source includes an RF energy frequency synthesizer coupled by electronic signal gate means amplifier which is connected to the acoustic transducer means, and the computing means includes a microprocessor and memory means for applying sequential pulsed control signals to the RF frequency synthesizer to predeterminedly vary the frequency of the RF energy applied to the acousto-optic tunable filter, and wherein control signals are applied to the electronic signal gate means to provide pulse width modulated RF energy to the RF amplifier.

4. An improved broad-band automated acousto-optic tunable filter multi-gas infra-red analyzer system comprising:

means for directing infra-red radiation through an environment of interest containing species to be analyzed, which species have predetermined infra-red absorption characteristics;

an acousto-optic tunable filter comprising an optically aligned acousto-optic thallium-arsenic-selenide crystal through which the infra-red radiation is passed at a predetermined angle relative to the crystal optic axis, an acoustic transducer means coupled to a variable frequency RF energy source and to the acousto-optic crystal to launch acoustic waves in the crystal to interact with a selected narrow bandwidth portion of the radiation to make the selected narrow bandwidth portion distinguishable from the remaining infrared radiation, which selected narrow bandwidth portion is a function of the frequency of the RF energy and acoustic waves, said selected narrow bandwidth portion being made distinguishable by being angularly displaced with respect to the non-selected infra-red radiation passed through said acousto-optic tunable filter;

means for directing the infra-red radiation upon said acousto-optic tunable filter prior to modification of the infra-red radiation by the absorption characteristics of a given species within the environment of interest;

infra-red radiation detection means which detects the angularly displaced, selected narrow bandwidth portion of the infra-red radiation after the angularly displaced selected narrow bandwidth portion has passed through the environment of interest, and which detection means generates an output electrical signal as a function of the detected radiation said detection means being disposed in relation to said acousto-optic tunable filter such that the angular displacement of the selected narrow bandwidth portion is adequate to separate it spatially from the broad-band non-selected radiation at said detection means; and computing means to which the detection means output electrical signal is applied for determining the species present in the environment of interest, and including means for the pulsed operation of the RF energy source to determine the timing and frequency of RF energy applied to the acoustic transducer means mated to the acouto-optic crystal to determine the infra-red wavelength selectivity or tuning of the acousto-optic tunable filter, wherein the pulsed operation permits discrimination by said detection means between pulsed emission means of the selected narrow bandwidth portion and emissions from the environment of interest.

5. The improved analyzer system set forth in claim 4 wherein the computing means includes a microprocessor and memory means for comparing the detected signal to predetermined molecular species indicative signals stored in the memory means, and wherein the memory means provides a predetermined sequence of signals which are applied to the microprocessor to be applied to a frequency synthesizer to vary the frequency of the RF energy applied to the acoustic transducer means coupled to the acousto-optic crystal to vary the selection of the narrow bandwidth portion of the infra-red radiation which is analyzed, and wherein predetermined frequencies corresponding to predetermined molecular sample species are applied.

6. The improved analyzer system set forth in claim 4 wherein the RF energy source includes an RF energy frequency synthesizer coupled by electronic signal gate means amplifier which is connected to the acoustic transducer means, and the computing means includes a microprocessor and memory means for applying sequential pulsed control signals to the RF frequency synthesizer to predeterminedly vary the frequency of the RF energy applied to the acousto-optic tunable filter, and wherein control signals are applied to the electronic signal gate means to provide pulse width modulated RF energy to the RF amplifier.

* * * * *